United States Patent [19]

Roe

[11] Patent Number: 5,342,338

[45] Date of Patent: Aug. 30, 1994

[54] DISPOSABLE ABSORBENT ARTICLE FOR LOW-VISCOSITY FECAL MATERIAL

[75] Inventor: Donald C. Roe, West Chester, Ohio

[73] Assignee: The Procter & Gamble Company, Cincinnati, Ohio

[21] Appl. No.: 76,713

[22] Filed: Jun. 11, 1993

[51] Int. Cl.⁵ .................... A61F 13/15; A61F 13/20
[52] U.S. Cl. ................... 604/383; 604/358; 604/378; 604/385.1
[58] Field of Search ............... 604/358, 378, 385.1, 604/366, 369, 370, 374–375, 381–383

[56] References Cited

U.S. PATENT DOCUMENTS

| | | |
|---|---|---|
| 3,890,973 | 6/1975 | Davis et al. . |
| 4,047,531 | 9/1977 | Karami . |
| 4,055,180 | 10/1977 | Karami . |
| 4,324,247 | 4/1982 | Aziz ........................ 604/378 |
| 4,397,644 | 8/1983 | Matthews et al. . |
| 4,643,727 | 2/1987 | Rosenbaum . |
| 4,673,402 | 6/1987 | Weisman et al. . |
| 4,699,823 | 10/1987 | Kellenberger et al. . |
| 4,704,112 | 11/1987 | Suzuki et al. . |
| 4,723,953 | 2/1988 | Rosenbaum et al. . |
| 4,798,603 | 1/1989 | Meyer et al. . |
| 4,885,204 | 12/1989 | Bither et al. . |
| 4,892,536 | 1/1990 | DesMarais et al. . |
| 4,908,026 | 3/1990 | Sukiennik ................... 604/378 |
| 4,968,312 | 11/1990 | Khan . |
| 4,990,147 | 2/1991 | Freeland . |
| 5,037,409 | 8/1991 | Chen et al. . |
| 5,037,416 | 8/1991 | Allen et al. . |
| 5,062,840 | 11/1991 | Holt et al. . |
| 5,124,197 | 6/1992 | Bernardin et al. . |
| 5,134,007 | 7/1992 | Reising et al. . |
| 5,143,779 | 9/1992 | Newkirk et al. . |
| 5,147,343 | 9/1992 | Kellenberger . |
| 5,171,236 | 12/1992 | Dreier et al. . |
| 5,192,606 | 3/1993 | Proxmire et al. . |
| 5,204,158 | 4/1993 | Phillips et al. . |
| 5,244,711 | 9/1993 | Drelich et al. . |

FOREIGN PATENT DOCUMENTS

| | | |
|---|---|---|
| 0059498A1 | 9/1982 | European Pat. Off. . |
| 0160569A2 | 11/1985 | European Pat. Off. . |
| 0160572A2 | 11/1985 | European Pat. Off. . |
| 0355740A2 | 2/1990 | European Pat. Off. . |
| 4-221556 | 8/1992 | Japan . |
| 5-49659 | 3/1993 | Japan . |
| WO93/03699 | 3/1993 | PCT Int'l Appl. . |
| 2103933A | 3/1983 | United Kingdom . |

Primary Examiner—Randall L. Green
Assistant Examiner—P. Zuttarelli
Attorney, Agent, or Firm—Larry L. Huston; Monte D. Witte; E. Kelly Linman

[57] ABSTRACT

A disposable absorbent article, such as a diaper. The disposable absorbent article has a first topsheet with apertures large enough for low-viscosity fecal material to pass through to a secondary topsheet. The secondary topsheet immobilizes the fecal material in position for dewatering, so that the liquid components of the fecal material are absorbed by the core and the solid components of the fecal material are separated from the liquid components. This arrangement provides for easier cleaning of the wearer when the soiled disposable absorbent article is removed.

16 Claims, 6 Drawing Sheets

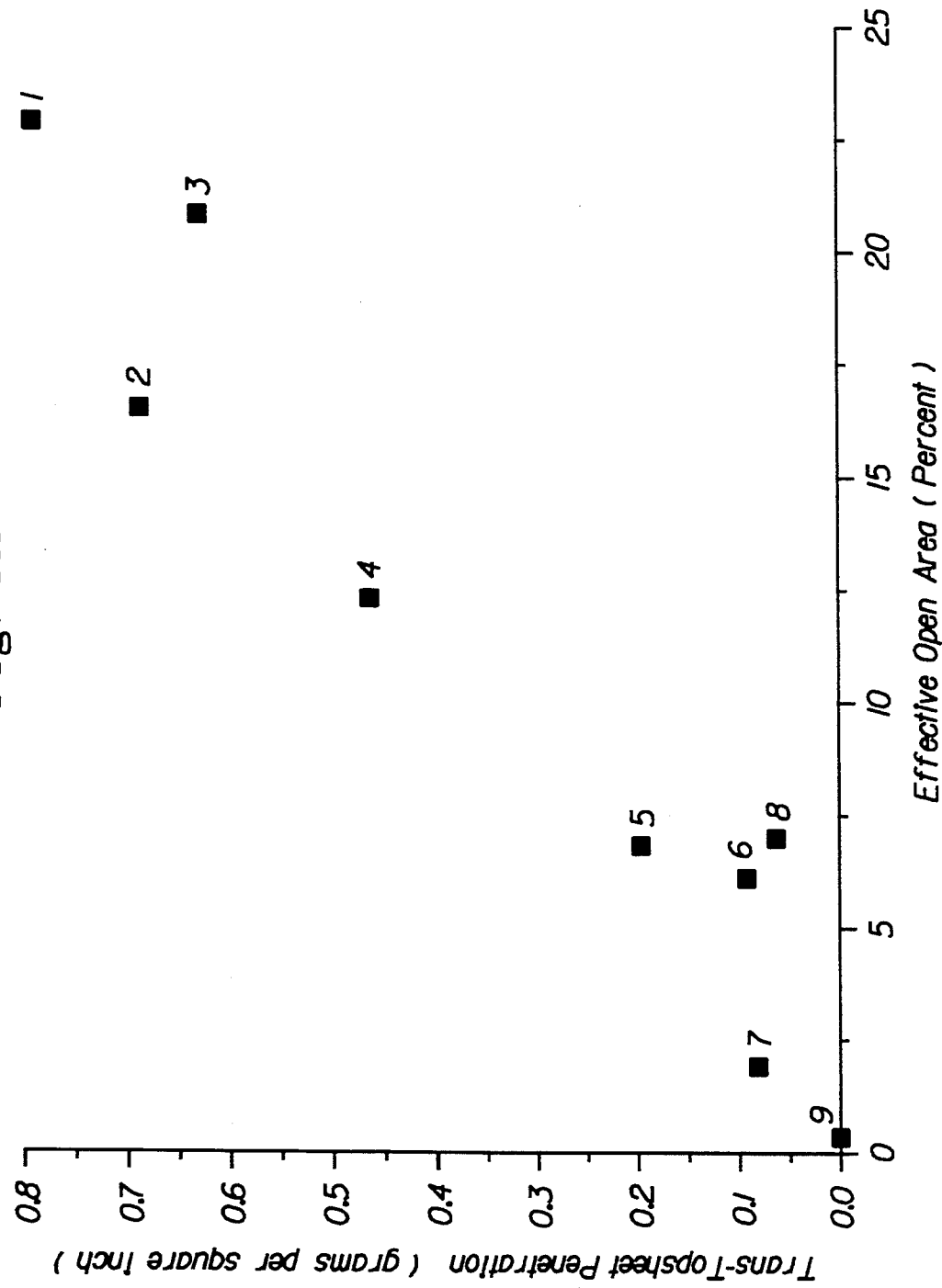

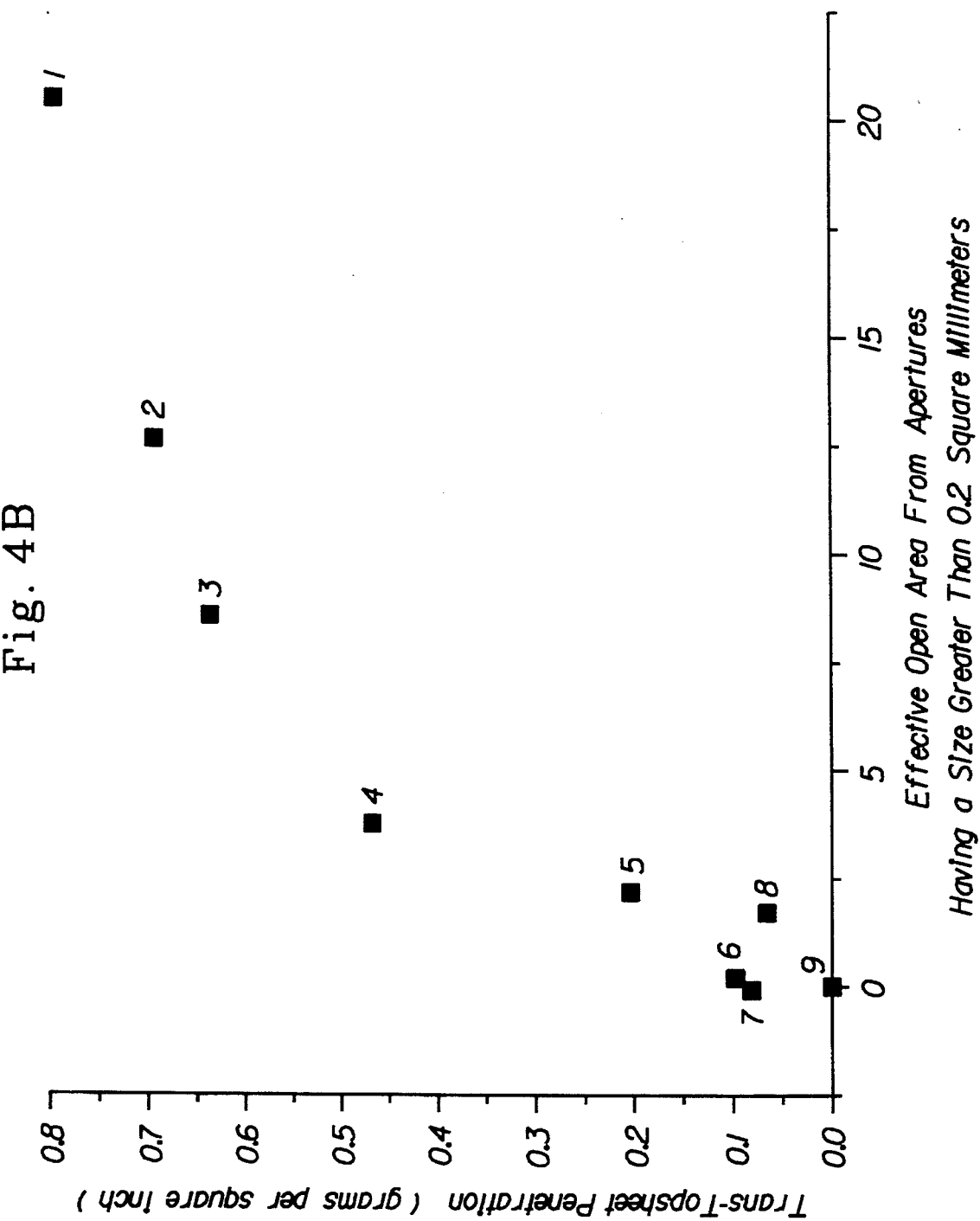

DISPOSABLE ABSORBENT ARTICLE FOR LOW-VISCOSITY FECAL MATERIAL

FIELD OF THE INVENTION

This invention relates to disposable absorbent articles, such as diapers and adult incontinence products, and more particularly to disposable absorbent articles which immobilize low-viscosity fecal material in order to make it easier to clean the wearer when the soiled disposable absorbent article is removed.

BACKGROUND OF THE INVENTION

Disposable absorbent articles such as diapers and adult incontinence products are well known in the prior art. Such disposable absorbent articles collect and retain urine and fecal material deposited thereon by the wearer.

To date, most attempts in the prior art to treat the urine and fecal material collected and retained on the disposable absorbent article have been directed to handling urine insults. Dealing with fecal material collected by the disposable absorbent article is simply more difficult than dealing with urine insults, due to the complex rheology of low-viscosity fecal material.

Exemplary of the urine handling prior art are several attempts to provide disposable absorbent articles having a first topsheet which faces towards and contacts the body of the wearer, and a layer under the first topsheet, hereinafter referred to as a "secondary topsheet" which either absorbs urine, or transfers the urine to an underlying core for storage until the disposable absorbent article is removed from the wearer.

Typically, the first topsheet and secondary topsheet have different material properties. The secondary topsheet may have a smaller pore size than the first topsheet to assist in transfer of the urine through the topsheet. The first topsheet may be hydrophobic and more resilient when wetted than the secondary topsheet, in order to pass fluids through the topsheet to the secondary topsheet.

In yet another attempt in the prior art, the disposable absorbent article has a first topsheet, secondary topsheet and core. The secondary topsheet consists essentially of meltblown hydrophilic fibers and has a pore size greater than the pore size of the core. This arrangement allegedly allows the secondary topsheet to rapidly receive multiple liquid insults and distribute the liquid in the X-Y plane prior to absorption by the core. In yet another attempt vertical wicking capability for urine has been attempted, by using inflated cellulose fibers which are free of a surface finish or are crosslinked to one another.

In another attempt in the prior art, an absorbent core suitable for acquiring and containing liquids such as urine in a particularly effective and efficient manner comprises multiple layers. The first layer, which is closest to the wearer, comprises hydrophilic fibrous material and has an acquisition zone of a relatively lower average density than other portions of this layer, in order to quickly acquire discharged liquids. Below the first layer is a liquid handling layer comprising a resilient, low density high void volume material that is moisture insensitive in order to rapidly acquire liquid insults into itself through the acquisition zone and distribute these liquids throughout the liquid handling layer to a storage layer. The storage layer comprises a combination of fibrous material and discrete particles of absorbent gelling material, and allows the liquid handling layer to be drained of the liquids it has acquired, so that the liquid handling layer may have sufficient capacity to acquire and distribute subsequent loadings of liquids.

Of course, absorbent gelling materials are also now well known in the prior art. Absorbent gelling materials are polymeric materials capable of absorbing large quantities of fluids such as urine and retaining such absorbed fluids under moderate pressure. The effectiveness of the absorbent gelling materials is quite dependent upon the form, position and weight percentage of absorbent gelling materials which are incorporated into the core of the disposable absorbent article.

Attempts to optimize the use of absorbent gelling materials to aid in the acquisition and retention of urine include disposing a fluid storage lower layer of an absorbent core underneath an upper larger fluid acquisition/distribution layer. The storage layer has about 75 percent of the absorbent gelling material found in the disposable absorbent article. The fluid acquisition/distribution layer contains little or no absorbent gelling material. The fluid acquisition/distribution layer has a particular density which is preferably less than that of the lower fluid storage layer. About 55 percent of the absorbent gelling material is found in the front half of the disposable absorbent article, and additionally about 75 percent of the absorbent gelling material in the lower layer is found in the front two-thirds of the disposable absorbent article.

Yet other attempts in the prior art distribute the absorbent gelling material particles in a continuous, non-step-wise positive concentration gradient. This gradient may be found throughout either the entire core or may be present only in at least a portion of the thickness of the core. In various embodiments, the absorbent gelling materials of such an attempt in the prior art may be generally centered in the absorbent core, or alternatively, may be disposed along the upper and lower surfaces of the core. In yet another attempt in the prior art, the absorbent gelling materials are allegedly dispersed among the pores wherein at least 50 percent of the absorbent gelling materials have a size greater than the median pore size of the core when it is wet.

Examples of such attempts in the prior art to handle urine include U.S. Pat. Nos. 4,047,531 issued Sep. 13, 1977 to Karami; commonly assigned 4,673,402 issued Jun. 16, 1987 to Weisman et al.; 4,699,823 issued Oct. 13, 1987 to Kellenberger et al.; 4,798,603 issued Jan. 17, 1989 to Meyer et al.; 5,037,409 issued Aug. 6, 1991 to Chen et al.; 5,124,197 issued Jun. 23, 1992 to Bernardin et al.; commonly assigned 5,134,007 issued Jul. 28, 1992 to Reising et al.; and 5,147,343 issued Sep. 15, 1992 to Kellenberger.

However, all of these attempts to handle urine do little, if anything, to improve handling of low-viscosity fecal material which may also be present in the disposable absorbent article. Attempts to deal with fecal material include providing a first topsheet which conforms closely to the wearer and has an aperture. The aperture is hopefully registered with the anal opening, so that fecal material passes therethrough and into a void space. The first topsheet may comprise various elastic panels in order to conform closely to the skin of the wearer, and/or may have linear elastic strands. Improvements have been made in this area of the prior art, such as optimizing the material properties of the first topsheet. Such optimization makes the first topsheet more comfortable to the wearer and allows a single disposable absorbent article to fit a larger range of sizes of wearers.

Yet other attempts have been made in the prior art to provide an absorbent core with a hole therein, in order to receive the fecal material. The hole may be oblate shaped, so that it is longer and narrower than the aperture in the first topsheet, or may be diamond shaped. The hole in the core may be positioned below an aperture which has elastic strips around its edge.

Improvements to this genre of prior art disposable absorbent articles also include the addition of spacers. Spacers may be interposed between the first topsheet and the core, in order to ensure a void space is present to receive the fecal material.

Yet other attempts have been made in the prior art to provide barriers which limit the movement of fecal material to particular portions of the disposable absorbent article. The barriers limit the contact of the fecal material to a lesser portion of the skin of the wearer, than a comparable disposable absorbent article which has no barriers.

Still other attempts in the prior art provide barrier leg cuffs which are upstanding from the plane of the topsheet. The barrier leg cuffs prevent fecal material from breaching the perimeter of the disposable absorbent article.

Examples of such attempts in the prior art to handle fecal material include commonly assigned U.S. Pat. No. 4,892,536 issued Jan. 9, 1990 to DesMarais et al.; U.S. Pat. No. 4,909,803 issued Mar. 20, 1990 to Aziz et al.; U.S. Pat. No. 4,968,312 issued Nov. 6, 1990 to Khan; commonly assigned U.S. Pat. No. 4,990,147 issued Feb. 5, 1991 to Freeland; commonly assigned U.S. Pat. No. 5,037,416 issued Aug. 6, 1991 to Allen et al.; U.S. Pat. No. 5,062,840 issued Nov. 5, 1991 to Holt et al.; commonly assigned U.S. Pat. No. 5,171,236 issued Dec. 15, 1992 to Dreier et al.; and European Patent Application 0,355,740 A2 published Feb. 28, 1990 to Enloe.

However, none of these attempts in the prior art to handle fecal material solve the problem of low-viscosity fecal material which is prevalent in younger children, particularly those who are breast fed. Low-viscosity fecal material easily migrates within the disposable absorbent article under the influences of gravity and motion or pressure by the wearer.

The migration of the fecal material often moves it towards the perimeter of the disposable absorbent article, increasing the likelihood of leakage. The migration of the fecal material also smears it against the skin of the wearer, making cleanup more difficult. In order to clean the wearer, the caretaker must wipe the entire area of the skin which has encountered the fecal material and typically has to deal with a relatively large soiled area.

Accordingly, it is an object of this invention to provide a disposable absorbent article which overcomes the disadvantages present in the prior art. Particularly, it is an object of this invention to provide a disposable absorbent article which reduces leakage of fecal material from the disposable absorbent article and minimizes the amount of low-viscosity fecal material remaining on the skin of the wearer once the disposable absorbent article is removed. It is further an object of this invention to provide a disposable absorbent article which separates the fecal material into components.

BRIEF SUMMARY OF THE INVENTION

The invention is a disposable absorbent article, such as a diaper, for being worn by a wearer. The disposable absorbent article comprises a liquid pervious first topsheet having a trans-topsheet penetration of at least 0.25 grams per square inch and a differential pressure of 0.071 pounds per square inch over a surface area of at least about 30 square inches, and preferably at least about 45 square inches. The minimum and preferred surface areas decrease in inverse relationship to the trans-topsheet penetration as it increases. For example, a first topsheet having a trans-topsheet penetration of at least 0.6 grams per square inch need only have this penetration occur over a minimum of four square inches.

Preferably, the disposable absorbent article further comprises a secondary topsheet intermediate the first topsheet and the core. If the secondary topsheet is included, it is bonded to less than 50 percent of the surface area of the first topsheet and is bonded to at least 50 percent of the surface area of the core. The secondary topsheet, if included, may be peripherally joined to the backsheet so that it would be unnecessary to join the first topsheet to the backsheet. The secondary topsheet has a trans-topsheet penetration of less than 0.20 grams per square inch at a differential pressure of 0.071 pounds per square inch. More preferably, the secondary topsheet has a trans-topsheet penetration of less than 0.15 grams per square inch.

The disposable absorbent article further has a liquid impervious backsheet at least partially peripherally joined to the first topsheet or to the secondary topsheet, and an absorbent core intermediate the first topsheet and the backsheet. The absorbent core is bonded to less than 50 percent of the surface area of the first topsheet.

BRIEF DESCRIPTION OF THE DRAWINGS

While the Specification concludes with claims pointing out and distinctly claiming the present invention, it is believed the same will be better understood by the following drawings taken in conjunction with the accompanying Specification wherein like components are given the same reference number and:

FIG. 4A is a two-dimensional graphical representation of the relationship between trans-topsheet penetration and percentage of effective open area;

FIG. 4B is a two-dimensional graphical representation of the relationship between trans-topsheet penetration and the percentage of total effective open area contributed by apertures having a size greater than 0.2 square millimeters;

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and adult incontinent persons and is worn about the lower torso of the wearer.

Figure 2:
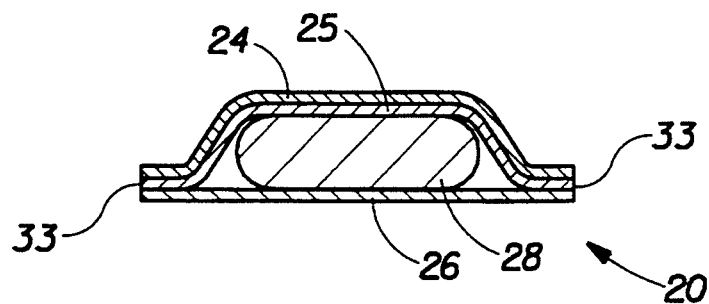
FIG. 2 is a vertical sectional view taken along line 2—2 of FIG. 1, showing the relationship of the first topsheet, secondary topsheet and core.
Figure 1:
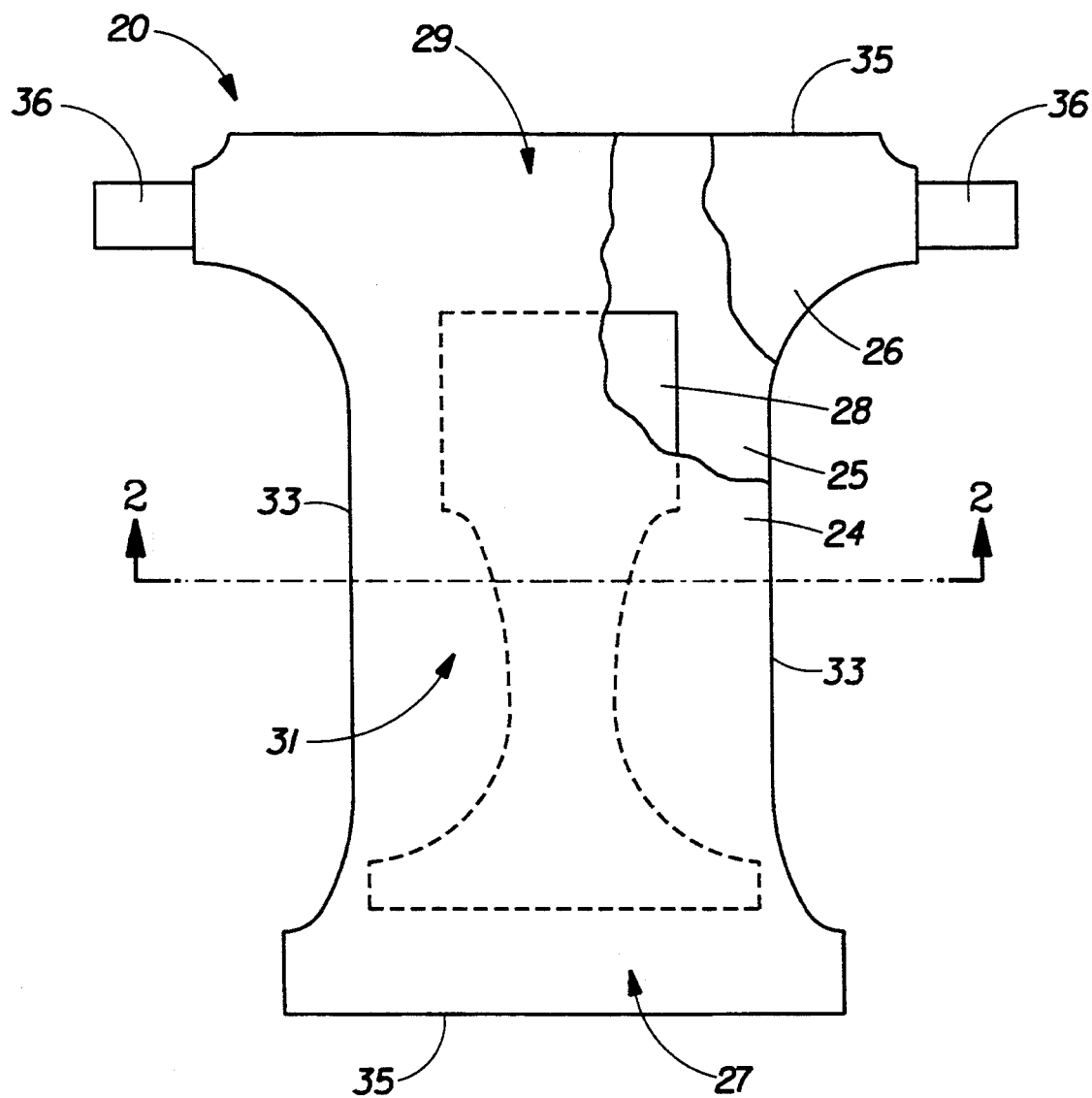
FIG. 1 is a top plan view, shown partially in cutaway, of a disposable absorbent article according to the present invention.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces or contacts the wearer, the inner surface, oriented towards the viewer. As shown in FIG. 1, the diaper 20 preferably comprises a liquid pervious first topsheet 24; a liquid impervious backsheet 26 joined with the first topsheet 24; an absorbent core 28 positioned between the first topsheet 24 and the backsheet 26; a liquid pervious secondary topsheet 25 positioned between the first topsheet 24 and the core 28. The diaper 20 may further comprise elasticized side panels (not shown); elasticized leg cuffs (not shown); an elastic waist feature (not shown); and a fastening system with tape tabs generally multiply designated as 36.

The diaper 20 is shown in FIG. 1 to have a first waist region 27 juxtaposed with the front of the wearer while the diaper 20 is being worn, a second waist region 29 opposed to the first waist region 27 and juxtaposed with the back of the wearer while the diaper 20 is being worn, a crotch region 31 positioned between the first waist region 27 and the second waist region 29, and a periphery which is defined by the outer edges of the diaper 20 in which the longitudinal edges are designated 33 and the end edges are designated 35. The inner surface of the diaper 20 comprises that portion of the diaper 20 which is positioned adjacent to the wearer's body during use (i.e., the inner surface generally is formed by at least a portion of the first topsheet 24 and other components joined to the first topsheet 24). The outer surface comprises that portion of the diaper 20 which is positioned away from the wearer's body (i.e., the outer surface generally is formed by at least a portion of the backsheet 26 and other components joined to the backsheet 26).

FIG. 1 shows an embodiment of the diaper 20 in which the first topsheet 24 and the backsheet 26 have length and width dimensions generally larger than those of the absorbent core 28. The first topsheet 24 and the backsheet 26 extend beyond the edges of the absorbent core 28 to thereby form the periphery of the diaper 20. Alternatively, the secondary topsheet 25 may extend beyond the edges of the core 28 and be joined to the backsheet 26 to form the periphery of the diaper 20. While the first topsheet 24, the secondary topsheet 25, the backsheet 26, and the core 28 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and U.S. patent application Ser. No. 07/715,152, allowed, "Absorbent Article With Dynamic Elastic Waist Feature Having A Predisposed Resilient Flexural Hinge", Kenneth B. Buell et al. filed Jun. 13, 1991; each of which is incorporated herein by reference.

The absorbent core 28 may be any absorbent means which is generally compressible, conformable, non-irritating to the wearer's skin, and capable of absorbing and retaining liquids such as urine and other certain body exudates. As shown in FIG. 1, the absorbent core 28 has a garment surface, a body surface, side edges, and waist edges. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may also be varied (e.g., the absorbent core 28 may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults.

Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference.

The backsheet 26 is positioned adjacent the garment surface of the absorbent core 28 and is preferably joined thereto by attachment means (not shown) such as those well known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.

For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents is incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body.

The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet 26 is a thermoplastic film having a thickness of from about 0.012 mm (0.5 mil) to about 0.051 mm (2.0 mils). Particularly preferred materials for the backsheet 26 include RR8220 blown films and RR5475 cast films as manufactured by Tredegar Industries, Inc. of Terre Haute, Ind. The backsheet 26 is preferably embossed and/or matte finished to provide a more clothlike appearance. Further, the backsheet 26 may permit vapors to escape from the absorbent core 28 (i.e., be breathable) while still preventing exudates from passing through the backsheet 26.

The first topsheet 24 and the secondary topsheet 25 each have two major faces. The first topsheet 24 has a first major face oriented towards the wearer and an opposed second major face oriented towards the secondary topsheet 25. The secondary topsheet 25 has a first major face oriented towards the first topsheet 24, and an opposed second major face oriented towards the core 28.

The first topsheet 24 is juxtaposed with, but not necessarily adjacent the body surface of the secondary topsheet 25, and is preferably joined to the backsheet 26 or secondary topsheet 25 such as those well known in the art. Suitable attachment means are described above with respect to joining the backsheet 26 to the absorbent core 28. In a preferred embodiment of the present invention, the first topsheet 24 and the backsheet 26 are joined directly to each other in the diaper periphery.

The first topsheet 24 is compliant, soft feeling, and non-irritating to the wearer's skin. Further, the first topsheet 24 is liquid pervious, permitting liquids (e.g., urine) to readily penetrate through its thickness. A suitable first topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the first topsheet 24 is made of a hydrophobic material to isolate the wearer's skin from liquids contained in the absorbent core 28. Alternatively, the topsheet 24 may be surfactant treated to make it hydrophilic.

There are a number of manufacturing techniques which may be used to manufacture the first topsheet 24. For example, the first topsheet 24 may be a nonwoven web of fibers spunbonded, carded, wet-laid, meltblown, hydroentangled, combinations or composite laminates of the above, or the like. Preferred first topsheets 24 include a carded/carded composite, hydroentangled over a wire forming screen and thermally air-through bonded by means well known to those skilled in the nonwovens art and hydro-formed films.

The first topsheet 24 has a minimum trans-topsheet penetration dependent upon the surface area of the first topsheet 24 having this minimum trans-topsheet penetration. Of course, the trans-topsheet penetration need not be the same throughout all areas of the first topsheet 24. The regions of the first topsheet 24 registered with the anal opening may have a relatively higher trans-topsheet penetration than the outlying regions of the first topsheet 24.

There is an inverse relationship between the minimum trans-topsheet penetration necessary to handle low-viscosity fecal material and the surface area of the first topsheet 24 having this minimum capacity. As a larger percentage of the first topsheet 24 surface area has a trans-topsheet penetration sufficient to handle low-viscosity fecal material, the necessary trans-topsheet penetration diminishes.

In any case, the first topsheet 24 should have a trans-topsheet penetration of at least about 0.25 grams per square inch providing at least 30 square inches of the first topsheet 24 has such a trans-topsheet penetration and preferably at least 45 square inches of the first topsheet 24 has such a trans-topsheet penetration. It is believed that a minimum of 4 square inches of the first topsheet 24, which are closely registered with the anal opening, are necessary to handle low-viscosity fecal material. If such a relatively small region of the first provided, this region of the first topsheet 24 should have a trans-topsheet penetration of at least about 0.50 and preferably at least about 0.60 grams per square inch.

The trade-off between trans-topsheet penetration and minimum surface area of the first topsheet 24 necessary to handle low-viscosity fecal material and the preferred surface area to handle low-viscosity fecal material for a diaper 20 having such a topsheet is illustrated in Table I below:

TABLE I

| Trans-topsheet Penetration (grams/square inch) | Minimum First Topsheet Surface Area Having This Trans-topsheet Penetration (square inches) | Preferred First Topsheet Surface Area Having This Trans-topsheet Penetration (square inches) |
| --- | --- | --- |
| 0.25 | 30 | 45 |
| 0.30 | 15 | 25 |
| 0.40 | 12 | 20 |
| 0.50 | 4 | 10 |
| 0.60 | 4 | 4 |

Figure 3:
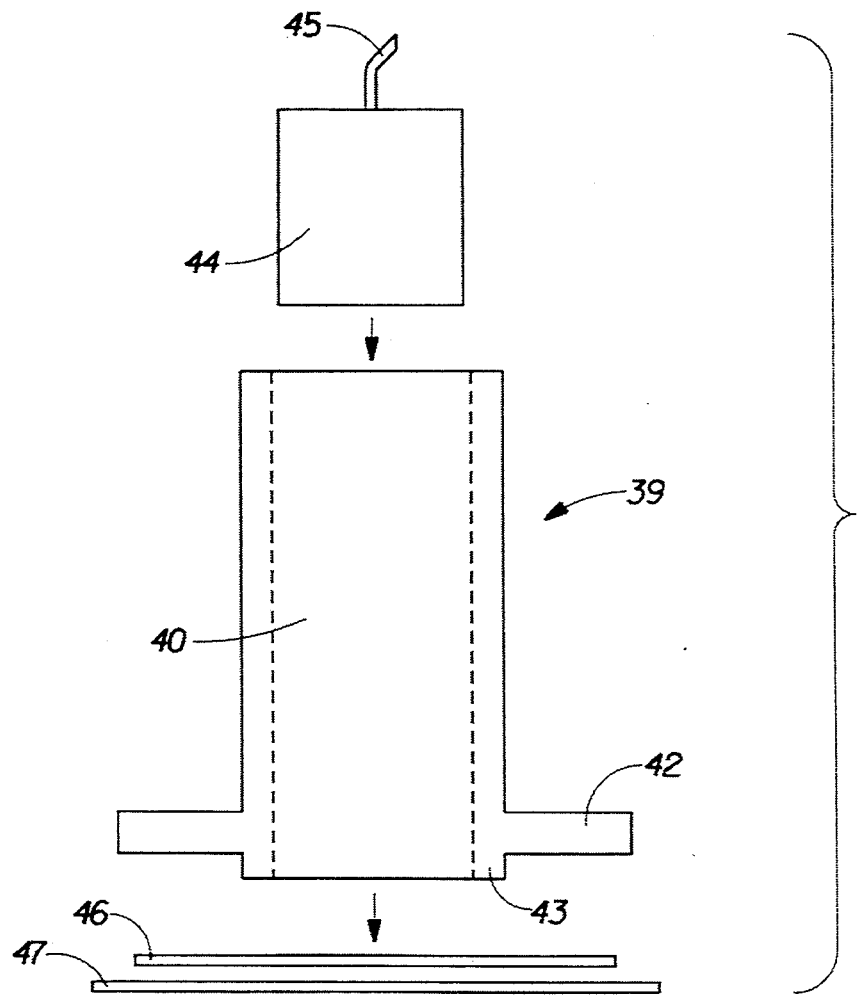
FIG. 3 is a schematic side elevational view of an apparatus which may be used to measure the trans-topsheet penetration of the first topsheet and the secondary topsheet.
Figure 3A:
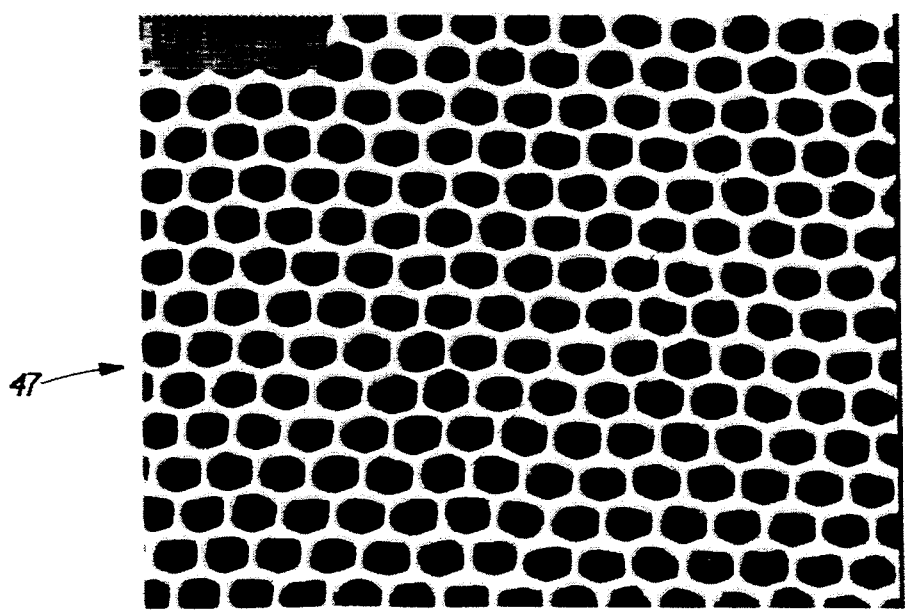
FIG. 3A is a top plan view of a photomicrograph of the substrate used to measure the trans-topsheet penetration.

Trans-topsheet penetration is measured by the following test. The apparatus 39 used for this measurement is illustrated in FIGS. 3 and 3A.

A hollow stainless steel cylinder 40 mounted on a plate 42 is provided. The stainless steel cylinder 40 has a height of 7.5 centimeters (2.95 inches), an inside diameter of 5.08 centimeters (2.00 inches) and an outside diameter of 6.3 centimeters (2.48 inches). The bottom of the cylinder 40 extends below the plate a distance of 3.5 millimeters, and has a lip with an annular thickness of 3.5 millimeters. The lip 43 prevents the fecal material analog, discussed below, from leaking outside the designated test area of the sample.

Also provided is a weight 44 of 100.6 grams. The weight 44 is also cylindrically shaped and has a diameter of 5.08 centimeters (2.0 inches), so that the weight 44 fits tightly within the cylinder 40 but can freely slide throughout the hole in the cylinder 40. This arrangement provides a pressure of 49.57 kilograms per square meter (0.071 pounds per square inch) and a test area of 3.142 square inches. If desired, the weight 44 may have a handle 45 to allow it to be easily inserted into and removed from the cylinder 40.

A sample 46 to be tested is provided. The sample 46 may be cut from an existing diaper 20 or may be supplied in raw material form. The sample 46 is cut to a 10.16 by 10.16 centimeters (4 by 4 inch) square size.

The substrate 47 and a high basis weight blotter are weighed to the nearest 0.01 grams. The sample 46 is then placed on a large cell vacuum formed film polyolefinic substrate 47. As illustrated in FIG. 3A, the substrate 47 preferably has elongated hexagonal apertures with a distance of about 4 millimeters between the furthest opposed flats, a distance of about 3 millimeters between the closest vertices, and is available from Tredegar Corporation of Terre Haute, Ind. under the designation X5790.

If the sample 46 is cut from a diaper 20, the sample should include only the first topsheet 24. The sample 46 should not include any portions of the secondary topsheet 25 or the absorbent core 28. Care must be taken when removing the sample 46 from the diaper 20 not to destroy the sample 46 or cause unintended gross deformation of the first topsheet 24. If difficulty is encountered in removing the sample 46 from the diaper 20, the sample 46 and the surrounding portion of the diaper 20 may be frozen. Freezing may be accomplished using PH100-15 circuit refrigerant made by Philips ECG, Inc. of Waltham, Mass.

The substrate 47 is, in turn, placed upon a high basis weight blotter (not shown). The high basis weight blotter is made of wet-laid 100% virgin cellulose fibers having a basis weight of 0.0925 grams per square inch and a caliper of about 0.75 millimeters (0.030 inches). A suitable blotter is number 989 filter paper made by Eaton-Dikeman Division of Knowlton Brothers of Mt. Holly Springs, Penn.

The cylinder 40 is centered on the sample 46. A syringe having an opening of 5 to 6 millimeters dispenses 10 cubic centimeters of test fluid through the hole in the cylinder 40 onto the top of the sample 46. The test fluid is an analog formulated as described below. The 100.6 gram weight 44 is inserted through the hole in the cylinder 40 and gently placed on the test fluid for a period of 2 minutes.

After 2 minutes the weight 44 is removed from the sample 46. The sample 46 is removed from the substrate 47 by dragging the sample 46 parallel to the substrate 47. Both the substrate 47 and the high basis weight blotter are then weighed. The trans-topsheet penetration is the increase in combined weight of the substrate 47 and the high basis weight blotter, caused by the test fluid penetrating through the sample 46 on a unit area basis, divided by the sample 46 test area of 3.142 square inches.

The test fluid is an analog made by mixing 3 percent by weight Carbopol 941 available from the B. F. Goodrich Corporation of Brecksville, Ohio, or an equivalent acrylic polymer, in distilled water for five minutes using a hand held electric mixer. The mixture is allowed to equilibrate for at least 12 hours and used for the trans-topsheet penetration test within 72 hours.

The first topsheet 24 may achieve the trans-topsheet capacities set forth in Table I, by having apertures with an effective aperture size of at least 0.2 square millimeters, and preferably at least 0.3 square millimeters. Effective apertures are those which have a gray level of 18 or less on a standard gray level scale of 0–255, under the image acquisition parameters described below.

The effective aperture size and percentage open area are determined by the following procedure using the image analysis system described below. The procedure has three principal steps: image acquisition, i.e., obtaining representative images of areas on the surface of the first topsheet 24; image measurement, i.e., measuring the percentage open area of an image and of individual apertures and their perimeters; and data analysis, i.e., exporting the percentage open area, individual aperture area, and perimeter measurements to a spreadsheet where frequency distributions, sum of area distributions, and hydraulic radius computations are made.

An image analysis system having a frame grabber board, microscope, camera and image analysis software is utilized. A model DT2855 frame grabber board available from Data Translation of Marlboro, Mass. is provided. A VH5900 monitor microscope, a video camera, having a VH50 lens with a contact type illumination head available from the Keyence Company of Fair Lawn, N.J. are also provided and used to acquire an image to be saved to computer file. The Keyence microscope acquires the image and the frame grabber board converts the analog signal of this image into computer readable digital format. The image is saved to computer file and measured using suitable software such as the Optimas Image Analysis software, version 3.1, available from the BioScan Company of Edmonds, Wash. In order to use the Optimas Image Analysis software, the computer should have Windows software, version 3.0 or later, available from the Microsoft Corporation of Redmond, Wash. and also have a CPU at least equivalent to the Intel 80386. Any suitable desk top PC may be used, with a 486 DX33 type PC having been found to be particularly suitable. Images being saved to and recalled from file were displayed on a Sony Trinitron monitor model PVM-1343MO with a final display magnification of about 50X.

The image acquisition step, noted above requires 10 different regions from a representative first topsheet 24 sample of a particular type of diaper 20 or from sample material to be tested. Each region is rectangular, measuring about 5.8 millimeters by 4.2 millimeters. The sample is placed on a black mat board to increase the contrast between the apertures and the portion of the sample which defines the apertures. The means gray level and standard deviation of the black mat board were 16 and 4, respectively.

Images are acquired with room lights off using the Keyence monitor microscope mounted on a copystand directly above the sample. The Keyence light source illuminating the sample is adjusted and monitored with the Optimas software to measure the mean gray level and standard deviation of a 0.3 density wedge on a Kodak Gray Scale available from Eastman Kodak Company of Rochester, N.Y. The control of Keyence light source is adjusted so that the mean gray level of the illuminated wedge is $111\pm1$ and the standard deviation is $10\pm1$. All images were acquired during a single time period, and the Keyence light source is monitored by measuring the mean gray level and standard deviation of the wedge throughout the image acquisition process.

In measuring an individual aperture, only the effective aperture size is of interest. Measuring the effective aperture size quantifies the aperture size intended to contribute to the porosity of the first topsheet 24, and account for contributions of fibers and fiber bundles which traverse an area intended to be an aperture. An effective aperture is any hole through the first topsheet 24 having a gray level less than or equal to 18 using image acquisition parameters as described herein. Thus, an intended aperture may be divided into plural effective apertures by traverse fibers.

The image analysis software is calibrated in millimeters by a ruler image acquired from the sample images. A 3 by 3 pixel averaging filter found in the Optimas 3.1 Image menu is applied to each saved image to reduce noise. The apertures are detected in the gray level range of 0 through 18. An aperture which is not fully contained within the 5.8 by $\pm 2$ viewing area is not considered in the individual area and perimeter measurements. Therefore area and perimeter averages and distributions are not affected by apertures which are not wholly contained within the field of view.

However, individual apertures which could not be fully viewed in the image are included in the percentage open area calculation. This difference occurs because the percent open area is simply the image of pixel ratios from 0 through 18 to the total number of pixels in the image. Areas having a gray level 19 or greater were not counted in the open area calculation.

The percentage open area for the average of 10 images for each first topsheet 24 is measured using the Optimas Image Analysis software. The percentage open area is defined as the ratio of the number of pixels having a gray level from 0 through 18 to the total number of pixels for the image. The percentage open area is measured for each image representing one particular region from a first topsheet 24 sample. The percentage open area from each of the 10 individual images is then averaged to yield a percentage open area for the entire sample.

The data analysis is conducted by an Excel spreadsheet, also available from the Microsoft Corporation of Redmond, Wash. The Excel spreadsheet organized the percentage open area, aperture area, and aperture perimeter measurements obtained from the Optimas software. Sample averages and standard deviations, size and frequency distributions of individual aperture areas and hydraulic radius computations (area divided by perimeter) for individual apertures are obtained using the spreadsheet.

Distributions of individual aperture area are also computed using the Excel spreadsheet. The apertures are sorted into bins of certain size ranges. The number of aperture areas falling into certain size ranges of interest is determined as well as the sum of the areas within each range. The ranges are set in increments of 0.05 square millimeters. These areas are expressed as a percentage of the total open area of the sample. The frequency and sum of the area distributions are obtained by combining individual aperture measurements from all 10 images for each sample.

The hydraulic radius for individual apertures is also computed by the Excel spreadsheet. The hydraulic radius is considered to be the individual aperture area divided by respective perimeter as taken from the Optimas software.

Once the hydraulic radii of the apertures is computed, a distribution for hydraulic radii within certain ranges may be easily determined. Additionally, a distribution for the hydraulic radii of apertures within certain size ranges may be easily determined.

Using the aforementioned procedure, trans-topsheet capacities percentage of effective open area contributed by apertures greater than 0.2 square millimeters and the average hydraulic radius of the apertures were determined. The results of this test are tabulated in Table II.

Table II below gives the trans-topsheet penetration (in grams per square inch) of prior art first topsheets taken from various commercially available diapers and of various commercially available prior art materials supplied for use as diaper 20 first topsheets 24. Also given are the trans-topsheet capacities of various materials for first topsheet 24 according to the claimed invention. The first column in Table II gives the commercial name of the product from which the first topsheet 24 was taken or the name of the first topsheet 24 material itself if the sample was not taken from a commercially available diaper. The second column gives the trans-topsheet penetration in grams per square inch. The third column gives the percentage of effective open area. The fourth column gives the effective open area from apertures greater than 0.2 square millimeters in size. The fifth column gives the average hydraulic radius of apertures having a size of 0.1 to 0.2 square millimeters.

TABLE II

| NAME | TRANS-TOPSHEET PENETRATION (GRAMS PER SQUARE INCH) | EFFECTIVE OPEN AREA (PERCENTAGE) | EFFECTIVE OPEN AREA FROM APERTURES GREATER THAN 0.2 SQUARE MILLIMETERS (PERCENTAGE) | AVERAGE HYDRAULIC RADIUS OF APERATURES FROM 0.1 TO 0.2 SQUARE MILLIMETERS (MILLIMETERS) |
| --- | --- | --- | --- | --- |
| 1. Pantex 18125X from Fater Corporation of Pescara, Italy | 0.791 | 22.5 | 20.48 | 0.0687 |
| 2. AMC 7191.26.1 from Fiberweb N.A. Simpsonville, SC | 0.688 | 16.21 | 12.64 | 0.0575 |
| 3. Always Sanitary Napkin* from The Procter & Gamble Company, Cincinnati, OH | 0.633 | 20.5 | 8.61 | 0.1011 |
| 4. ACC 7192.36.1 from Fiberweb N.A. Simpsonville, SC | 0.467 | 12.14 | 3.76 | 0.0625 |
| 5. Huggies Super Trim from Kimberly-Clark, Dallas, TX | 0.202 | 6.73 | 2.22 | 0.0617 |
| 6. Huggies Baby Steps from Kimberly-Clark, Dallas, TX | 0.098 | 6.04 | 0.24 | 0.0751 |
| 7. Pampers Phases from The Procter & Gamble Company, Cincinnati, OH | 0.084 | 1.94 | 0 | N/A |
| 8. ACC P0391.0 from Veratec Inc. Walpole, MA | 0.069 | 7 | 1.75 | 0.0589 |
| 9. Huggies Ultra Trim Baby Steps from Kimberly-Clark, Dallas, TX | 0 | 0.4 | 0 | N/A |

*This first topsheet 24 was made of Tredegar Company, Cincinnati, Ohio X5600 film having a thickness of 0.0016 inches prior to forming, instead of the conventional Always sanitary napkin first topsheet 24 film which has a thickness of 0.001 inches prior to forming.

As illustrated by Table II, there is a direct correlation between trans-topsheet penetration and effective open area. This correlation is discussed below relative to FIGS. 4A-5, which shows a lesser, but still direct correlation between trans-topsheet penetration and effective open area contributed by apertures having a size greater than 0.2 square millimeters. The numbering of the data points in FIGS. 4A-6 corresponds to the numbering used in Table II.

FIGS. 4A-4B generally demonstrate that effective open area contributed by smaller sized apertures does not specifically contribute to trans-topsheet penetration. FIGS. 4A and 4B show that as the percentage of effective open area increased, trans-topsheet penetration similarly increased. The data points having a trans-topsheet penetration less than or equal to 0.2 grams per square inches represent diapers and materials according to the prior art. The data points having a trans-topsheet penetration greater than 0.4 grams per square inch represent first topsheets 24 according to the present invention.

However, FIG. 4A illustrates a non-monotonic relationship between the percentage of effective open area and the trans-topsheet penetration. This non-monotonic relationship is apparent in both the prior art samples and the samples according to the present invention.

Referring to FIG. 4B, for apertures having a size greater than 0.2 square millimeters, the non-monotonic relationship vanishes for all of the samples according to the present invention and all but one of the samples according to the prior art. FIG. 4B thus illustrates that only effective apertures having a particular minimum size demonstrate efficacy in transmitting low-viscosity fecal material through the first topsheet 24. Preferably, a first topsheet 24 according to the present invention has apertures with a size of at least 0.1 square millimeters, and more preferably a size of at least 0.2 square millimeters.

Figure 5:
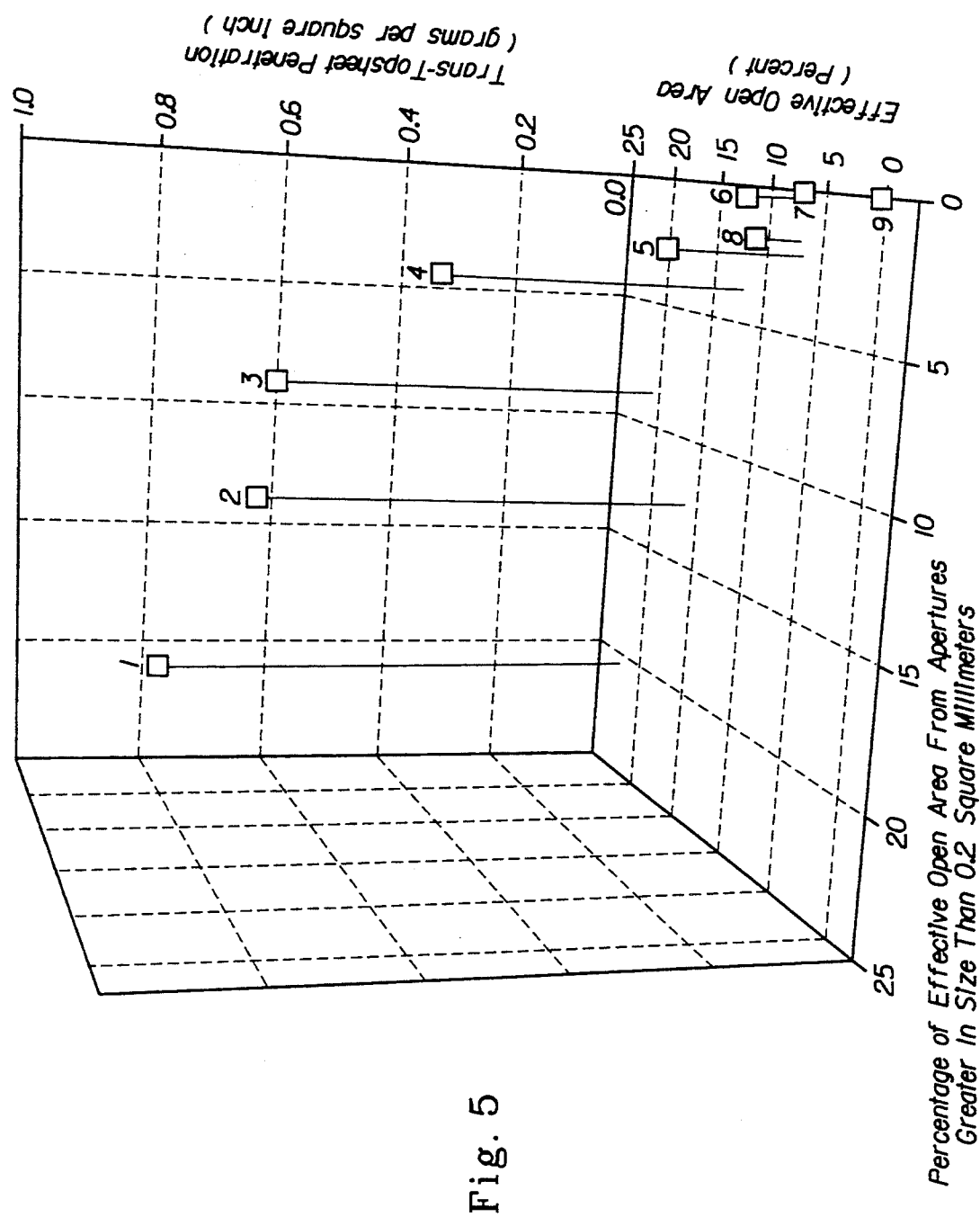
FIG. 5 is a three-dimensional graphical representation, taken from FIGS. 4A and 4B, of the interrelationship between trans-topsheet penetration, the percentage of effective open area, and the effective open area contributed by apertures having a size greater than 0.2 square millimeters.

Referring to FIG. 5, the aforementioned monotonic relationship is still present, however, it is seen that there is a weak relationship between total effective open area and the effective open area from apertures greater than 0.2 square millimeters in size. Accordingly, FIG. 5 confirms that how the percentage of effective open area is allocated among apertures of different sizes is a factor in the efficacy of the first topsheet 24 according to the present invention in transmitting low-viscosity fecal material.

Generally, for a given percentage effective open area, a greater aperture size is desirable in the first topsheet 24—in order to obtain a sufficient trans-topsheet penetration. Of course, the apertures should not be too large, otherwise fecal material will still reside against the skin of the wearer because the apertures do not effectively insulate the wearer from the fecal material after it passes through the first topsheet 24.

Referring to FIG. 4A, 4B, and 5 the first topsheet 24 in a disposable absorbent article according to the present invention preferably has the trans-topsheet capacities, listed in Table I above, achieved by having at least 12 percent effective open area, preferably at least 15 percent effective open area, and more preferably at least 20 percent effective open area.

Figure 6:
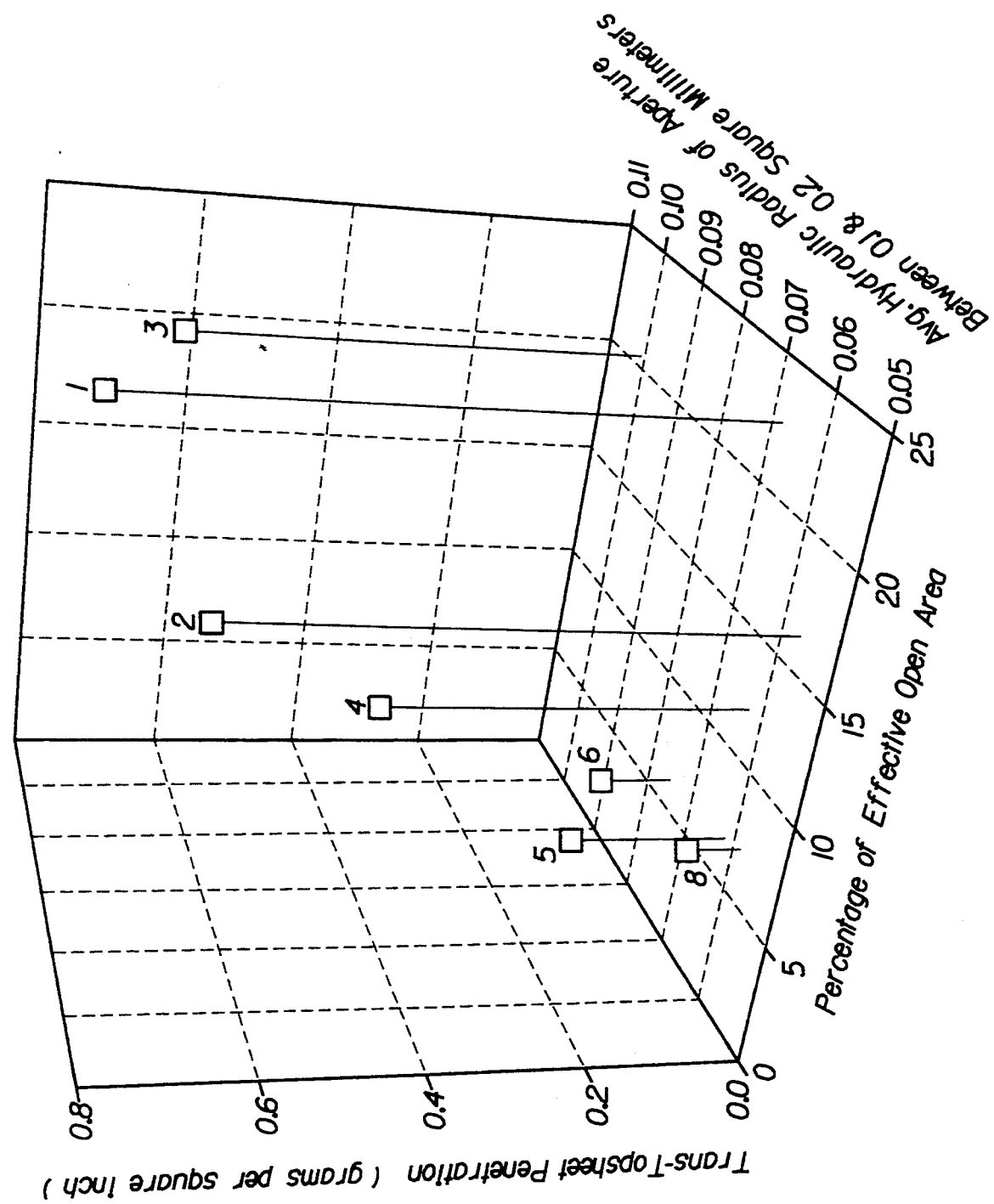
FIG. 6 is a three-dimensional graphical representation of the interrelationship between trans-topsheet penetration, the percentage of effective open area, and the average hydraulic radius of apertures between 0.1 and 0.2 square millimeters in size.

Referring to FIG. 6, it is seen that the shape of the aperture, as determined by its hydraulic radius also influences the trans-topsheet capacities. Generally, there is a direct correlation between the average hydraulic radius and the trans-topsheet penetration. FIG. 6 was limited to apertures having a size between 0.1 and 0.2 square millimeters, in order to reduce gross variations that would occur from the unlimited aperture size if the apertures much greater in size than 0.2 square millimeters were considered. Sample numbers 7 and 9 were not included in FIG. 6 because they had no apertures between 0.1 and 0.2 square millimeters in size.

With continuing reference to FIG. 6, it is seen that the average hydraulic radius of apertures having an effective size of 0.1 to 0.2 square millimeters is preferably at least 0.06 millimeters, more preferably at least 0.08 millimeters, and most preferably at least 0.10 millimeters.

A suitable first topsheet 24 may be provided in the form of a nonwoven web having a basis weight of approximately 28 grams per square meter (0.119 pounds per 3,000 square feet) and discrete apertures. Such a nonwoven web is available from Fiberweb Company of Simpsonville, S.C., as Number 7192.36.1.

The secondary topsheet 25 preferably has a trans-topsheet penetration of less than 0.20 grams per square inch, and more preferably a trans-topsheet penetration of less than 0.15 grams per square inch. It is important that the secondary topsheet 25 have a considerably lesser trans-topsheet penetration that the first topsheet 24, in order that the secondary topsheet 25 may readily receive fecal material which passes through the first topsheet 24 and immobilize and preferably dewater the fecal material. By immobilizing the fecal material underneath the first topsheet 24, the fecal material is less likely to migrate to the perimeter of the diaper 20 and cause leakage or remain on the wearer's skin.

Furthermore, if the fecal material is immobilized on the secondary topsheet 25 and under the first topsheet 24, the fecal material can be dewatered in this position. Dewatering the fecal material achieves the benefit of having less low-viscosity fecal material remain in contact with the skin of the wearer.

Such a secondary topsheet 25 may be provided in the form of a nonwoven web without discrete apertures and having a basis weight of approximately 18 grams per square meter (11.06 pounds per 3,000 square feet). Such a nonwoven fabric may be supplied from the Fiberweb Company of Simpsonville, S.C. as Model Number 66220.

The secondary topsheet 25 should be only peripherally joined to the first topsheet 24. At most, 50 percent of the secondary topsheet 25 within a minor peripheral region should be joined to the first topsheet 24. The secondary topsheet 25 is joined to the first topsheet 24 in only discrete localized regions inside the peripheral region, to maximize low-viscosity fecal material penetration and to minimize rewet. Rewet occurs when urine or the liquid components of fecal material return to the body facing side (i.e., the first major face) of the first topsheet 24 after the secondary topsheet 25 and core 28 become loaded.

If desired, the first topsheet 24 and the secondary topsheet 25 may be bonded together at sites within the periphery of the diaper 20. If such bonding occurs, preferably the bonding is done at discrete sites. Such bonding should be in a pattern which permits the first topsheet 24 to separate from the secondary topsheet 25 a Z-direction distance of about 0.5 to 7.6 centimeters (0.20 to 3.0 inches). If the bonding sites are too close together, they will create a damming effect, preventing low-viscosity fecal material which is entrapped between the first topsheet 24 and the secondary topsheet 25 from moving in the X-Y direction. In an extreme case, bonding sites which are too close together will prevent or substantially minimize penetration of the low-viscosity fecal material through the first topsheet 24. Alternatively, if the bonding sites are too far apart, excessive Z-direction separation between the first topsheet 24 and the secondary topsheet 25 will occur, allowing the diaper 20 to become unstable and lodge in the gluteal groove of the wearer.

A particularly preferred embodiment utilizes two longitudinally oriented stripes of discrete ultrasonic bonds. The discrete ultrasonic bonds have a diameter of about 2 millimeters. Each ultrasonic bond is longitudinally spaced from the adjacent ultrasonic bond on a pitch of about 0.3 centimeters (0.12 inches) and is arranged in a serpentine pattern. For the embodiments described herein, the two longitudinally oriented strips may be transversely separated by a distance of about 4 centimeters (1.5 inches) on a diaper 20 having a core 28 about 14 centimeters (5.51 inches) in transverse dimension.

Regardless of the bond pattern selected, preferably less than 50 percent and more preferably less than 25 percent of the surface area of the first topsheet 24 is joined to the secondary topsheet 25 between the leg cuffs or between the inner leg cuffs if the diaper 20 has dual leg cuffs.

Preferably a higher percentage of the surface area of the secondary topsheet 25 is joined to the absorbent core 28. If the secondary topsheet 25 is joined to the absorbent core 28, maximum dewatering of the fecal material can occur once the fecal material is immobilized. Preferably the secondary topsheet 25 is joined throughout at least 50 percent of its surface area to the absorbent core 28 by a bond pattern such as a reticulated narrow-bead hot melt adhesive.

The diaper 20 may further comprise elasticized leg cuffs (not shown) which provide improved containment of liquids and other body exudates. Each elasticized leg cuff may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper 20 which provides a contractible leg opening having a side flap and one or more elastic members to provide an elasticized leg cuff (gasketing cuff). Commonly assigned U.S. Pat. No. 4,909,803 entitled "Disposable Absorbent Article Having Elasticized Flaps" issued to Aziz et al. on Mar. 20, 1990, describes a disposable diaper 20 having "stand-up" elasticized flaps (barrier cuffs) to improve the containment of the leg regions. Commonly assigned U.S. Pat. No. 4,695,278 entitled "Absorbent Article Having Dual Cuffs" issued to Lawson on Sep. 22, 1987, describes a disposable diaper 20 having dual cuffs including a gasketing cuff and a barrier cuff.

The diaper 20 preferably further comprises an elastic waist feature (not shown) that provides improved fit and containment. The elastic waist feature is that portion or zone of the diaper 20 which is intended to elastically expand and contract to dynamically fit the wearer's waist. The elastic waist feature at least extends longitudinally outwardly from at least one of the waist edges of the absorbent core 28 and generally forms at least a portion of the end edge of the diaper 20. Disposable diapers are generally constructed so as to have two elastic waist features, one positioned in the first waist region 27 and one positioned in the second waist region 29, although diapers can be constructed with a single elastic waist feature. Further, while the elastic waist feature or any of its constituent elements can comprise a separate element affixed to the diaper 20, the elastic waist feature is preferably constructed as an extension of other elements of the diaper 20 such as the backsheet 26 or the first topsheet 24, preferably both the backsheet 26 and the first topsheet 24. The elasticized waistband 34 may be constructed in a number of different configurations including those described in U.S. Pat. No. 4,515,595 issued to Kievit et al. on May 7, 1985 and the above referenced U.S. patent application Ser. No. 07/715,152; each of these references being incorporated herein by reference.

The diaper 20 also comprises a fastening system 36 which forms a side closure which maintains the first waist region 27 and the second waist region 29 in an overlapping configuration such that lateral tensions are maintained around the circumference of the diaper 20 to maintain the diaper 20 on the wearer. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; commonly assigned U.S. Pat. No. 4,946,527 entitled "Pressure-Sensitive Adhesive Fastener And Method of Making Same" issued to Battrell on Aug. 7, 1990; commonly assigned U.S. Pat. No. 3,848,594 entitled "Tape Fastening System for Disposable Diaper" issued to Buell on Nov. 19, 1974; commonly assigned U.S. Pat. No. 4,662,875 entitled "Absorbent Article" issued to Hirotsu et al. on May 5, 1987; and the hereinbefore referenced U.S. patent application Ser. No. 07/715,152; each of which is incorporated herein by reference.

The diaper 20 is preferably applied to a wearer by positioning one of the waist regions 27, 29 preferably the second waist region 29, under the wearer's back and drawing the remainder of the diaper 20 between the wearer's legs so that the other waist region, preferably the first waist region 27, is positioned across the front of the wearer. The tape tabs 36 of the fastening system are then released from the release portion. The diaperer then wraps the elasticized side panel around the wearer, while still grasping the tab portion. The fastening system is secured to the outer surface of the diaper 20 to effect two side closure.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article for being worn by a wearer, said disposable absorbent article comprising:
   a liquid pervious first topsheet, said first topsheet having a trans-topsheet penetration of at least about 0.25 grams per square inch;
   an absorbent core intermediate said first topsheet and said backsheet;
   a secondary topsheet intermediate said first topsheet and said core, said secondary topsheet having two major faces, a first major face oriented towards said first topsheet and a second major face oriented towards said core, wherein less than fifty percent of the surface area of said first major surface of said secondary topsheet is bonded to said first topsheet and at least fifty percent of the surface area of said second major surface of said secondary topsheet is bonded to said core, said secondary topsheet having a trans-topsheet penetration less than about 0.20 grams per square inch; and
   a liquid impervious backsheet at least partially peripherally joined to one of said first topsheet and said secondary topsheet.

2. A disposable absorbent article according to claim 1 wherein a first topsheet has a trans-topsheet penetration of at least about 0.40 grams per square inch.

3. A disposable absorbent article according to claim 2 wherein said first topsheet has a trans-topsheet penetration of at least about 0.60 grams per square inch.

4. A disposable absorbent article according to claims 1, 2 or 3 wherein at least about 4 square inches of said first topsheet has said trans-topsheet penetration.

5. A disposable absorbent article according to claim 4 wherein at least about 20 square inches of said first topsheet has said trans-topsheet penetration.

6. A disposable absorbent article according to claim 5 wherein said first topsheet and said second topsheet are bonded together, at discrete sites spaced apart at least about 0.5 inches.

7. A disposable absorbent article according to claims 1, 2 or 3 wherein said first topsheet has an effective open area of at least about 15 percent.

8. A disposable absorbent article according to claim 7 wherein said first topsheet has a plurality of apertures with an effective size between 0.1 and 0.2 square millimeters.

9. A disposable absorbent article according to claim 8 wherein said first topsheet has a plurality of apertures with an effective size greater than 0.2 square millimeters.

10. A disposable absorbent article according to claim 8 wherein a plurality of said apertures have an average hydraulic radius of at least about 0.06 millimeters.

11. A disposable absorbent article for being worn by a wearer, said disposable absorbent article comprising:
    a liquid pervious first topsheet, said first topsheet having a trans-topsheet penetration of at least about 0.50 grams per square inch;
    an absorbent core intermediate said first topsheet and said backsheet;
    a secondary topsheet intermediate said first topsheet and said core, said secondary topsheet having two major faces, a first major face oriented towards said first topsheet and a second major face oriented towards said core, wherein less than fifty percent of the surface area of said first major surface of said secondary topsheet is bonded to said first topsheet and at least fifty percent of the surface area of said second major surface of said secondary topsheet is bonded to said core, said secondary topsheet having a trans-topsheet penetration less than than about 0.20 grams per square inch; and a liquid impervious backsheet at least partially peripherally joined to one of said first topsheet and said secondary topsheet.

12. A disposable absorbent article according to claim 11 wherein at least 4 square inches of said first topsheet has said trans-topsheet penetration.

13. A disposable absorbent article according to claim 12 wherein at least 10 square inches of said first topsheet has said trans-topsheet penetration.

14. A disposable absorbent article according to claim 12 wherein said first topsheet has an effective open area of at least about 12 percent.

15. A disposable absorbent article according to claim 14 wherein said first topsheet has an effective open area of at least about 15 percent.

16. A disposable absorbent article according to claim 14 wherein said first topsheet has a plurality of apertures with a size greater than 0.2 square millimeters.

* * * * *

UNITED STATES PATENT AND TRADEMARK OFFICE
CERTIFICATE OF CORRECTION

PATENT NO. : 5,342,338
DATED : AUGUST 30, 1994
INVENTOR(S) : ROE

It is certified that error appears in the above-indentified patent and that said Letters Patent is hereby corrected as shown below:

| | |
|---|---|
| Column 8, line 60 | before "provided" insert therefor --topsheet 24 is--. |
| Column 11, line 20 | delete "means" and insert therefor --mean--. |
| Column 11, line 56 | delete "±" and insert therefor --4.2--. |
| Column 15, line 32 | delete "that" and insert therefor --than--. |
| Column 16, line 24 | delete "strips" and insert therefor --stripes--. |
| Column 19, line 1 | delete second occurrence of the word "than." |

Signed and Sealed this

Twenty-fifth Day of April, 1995

*Attest:*

BRUCE LEHMAN

*Attesting Officer*     *Commissioner of Patents and Trademarks*